(12) United States Patent
De La Serna et al.

(10) Patent No.: US 7,011,649 B2
(45) Date of Patent: Mar. 14, 2006

(54) COLLAPSIBLE SYRINGE CARTRIDGE

(75) Inventors: Pedro E. De La Serna, San Jose, CA (US); Scott J. Gilbert, Menlo Park, CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 10/291,312

(22) Filed: Nov. 8, 2002

(65) Prior Publication Data
US 2003/0236502 A1 Dec. 25, 2003

Related U.S. Application Data

(60) Provisional application No. 60/337,681, filed on Nov. 9, 2001.

(51) Int. Cl.
A61M 5/32 (2006.01)
(52) U.S. Cl. .................................................. 604/197
(58) Field of Classification Search ............ 604/131, 604/139, 134, 156, 135, 157, 136, 196, 137, 604/197, 138, 198
See application file for complete search history.

(56) References Cited

U.S. PATENT DOCUMENTS

| | | | | |
|---|---|---|---|---|
| 2,752,918 A | * | 7/1956 | Uytenbogaar | 604/136 |
| 3,403,680 A | * | 10/1968 | Watson et al. | 604/138 |
| 3,797,489 A | | 3/1974 | Sarnoff | |
| 4,031,889 A | | 6/1977 | Pike | |
| 5,137,516 A | * | 8/1992 | Rand et al. | 604/136 |
| 5,176,645 A | | 1/1993 | Guerro | |
| 5,300,030 A | * | 4/1994 | Crossman et al. | 604/136 |
| 5,328,481 A | | 7/1994 | Wang | |
| 5,352,196 A | | 10/1994 | Haber et al. | |
| 5,425,715 A | * | 6/1995 | Dalling et al. | 604/136 |
| 5,520,639 A | | 5/1996 | Peterson et al. | |
| 5,527,287 A | | 6/1996 | Miskinyar | |
| 5,741,275 A | | 4/1998 | Wyssmann | |
| 5,779,677 A | * | 7/1998 | Frezza | 604/134 |
| 5,792,099 A | | 8/1998 | DeCamp et al. | |
| 5,845,811 A | | 12/1998 | Shervington et al. | |
| 6,047,865 A | | 4/2000 | Shervington et al. | |
| 6,270,479 B1 | | 8/2001 | Bergens et al. | |
| 6,447,482 B1 | * | 9/2002 | R.o slashed.nborg et al. | 604/131 |

(Continued)

FOREIGN PATENT DOCUMENTS

EP 0 295 917 A 12/1988

(Continued)

OTHER PUBLICATIONS

International Search Report dated May 28, 2003 from International Application No. PCT/US/ 02/35876.

(Continued)

Primary Examiner—Manuel Mendez
(74) Attorney, Agent, or Firm—Angela N. Nwaneri

(57) ABSTRACT

The present invention provides a syringe cartridge that is sufficiently robust to be used in autoinjectors that generate injection forces sufficient to deliver viscous medicaments. The syringe cartridge of the present invention includes a syringe, a bias mechanism, and a casing. The casing of the syringe cartridge of the present invention includes a collapsible portion and a fixed portion. Advantageously, the collapsible portion of the casing collapses within the fixed portion of the casing as the syringe is driven through its stroke within the syringe cartridge. As the collapsible portion collapses within the fixed portion, the length of the syringe cartridge is effectively reduced, which, in turn, allows the use of a shorter plunger and thereby facilitates the construction of a more compact autoinjector.

18 Claims, 6 Drawing Sheets

U.S. PATENT DOCUMENTS

| | | | |
|---|---|---|---|
| 6,569,123 B1 * | 5/2003 | Alchas et al. ............... | 604/192 |
| 2001/0005781 A1 | 6/2001 | Bergens et al. | |

FOREIGN PATENT DOCUMENTS

| EP | 0 897 728 A1 | 2/1999 |
|---|---|---|
| HU | 179577 B | 11/1982 |
| HU | 186718 B | 9/1985 |
| HU | 214350 B | 3/1988 |
| HU | 195428 B | 5/1988 |
| HU | 189198 B | 6/1990 |
| HU | 211712 B | 12/1995 |
| HU | 218191 B | 6/2000 |
| WO | WO 94 13342 A | 6/1994 |
| WO | WO 95/31235 | 11/1995 |
| WO | WO 99/06100 | 2/1999 |
| WO | WO 01/64269 | 9/2001 |

OTHER PUBLICATIONS

Novelty search report in Hungarian application No. P0401926.

Novelty search report in Hungarian application No. P0402648.

* cited by examiner

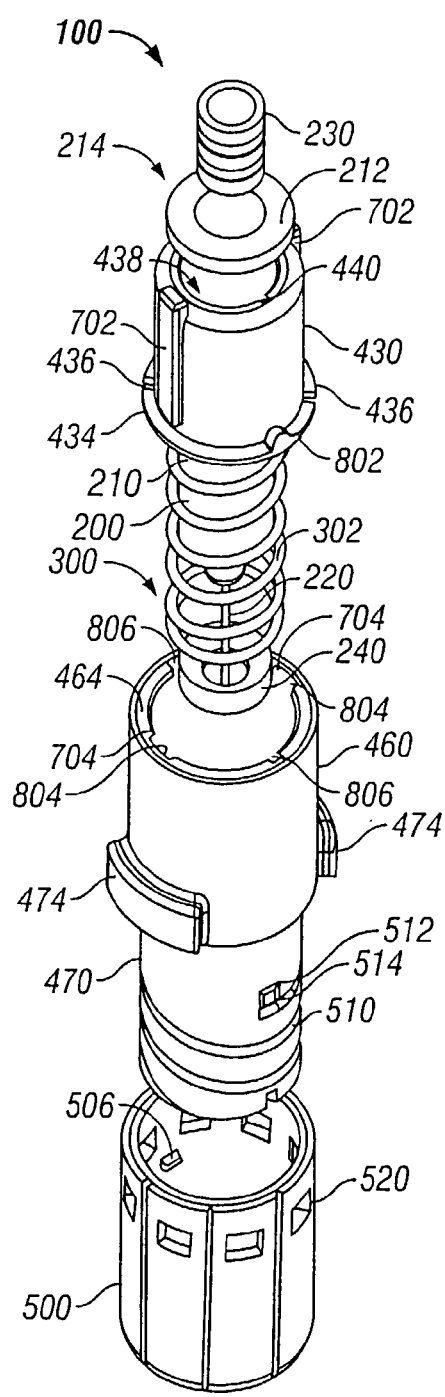
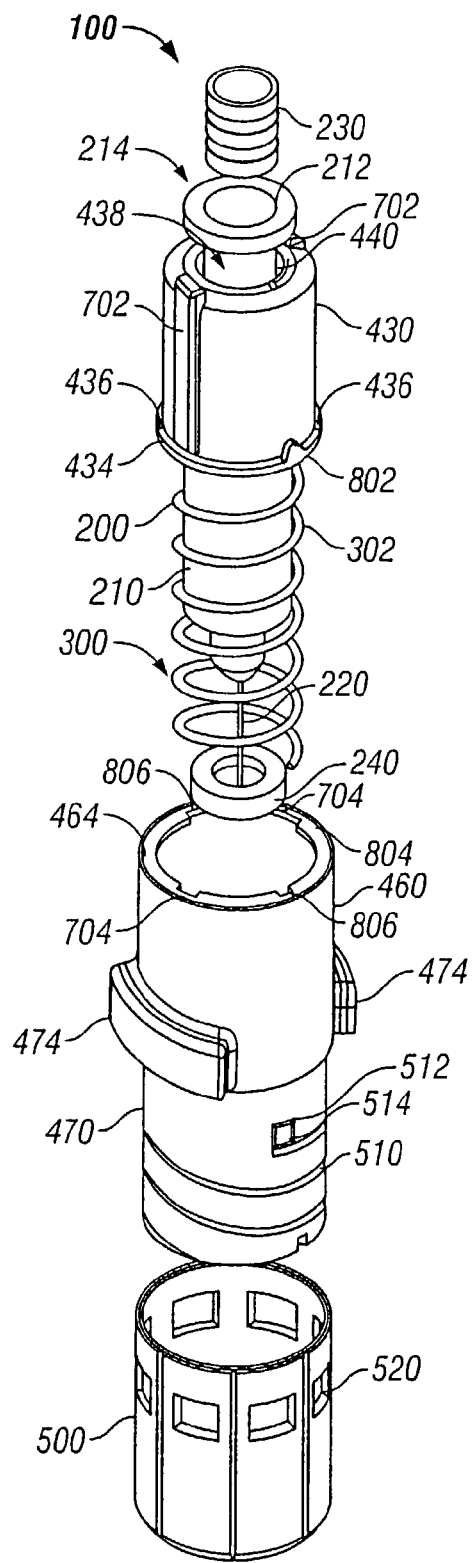
FIG. 9
FIG. 10

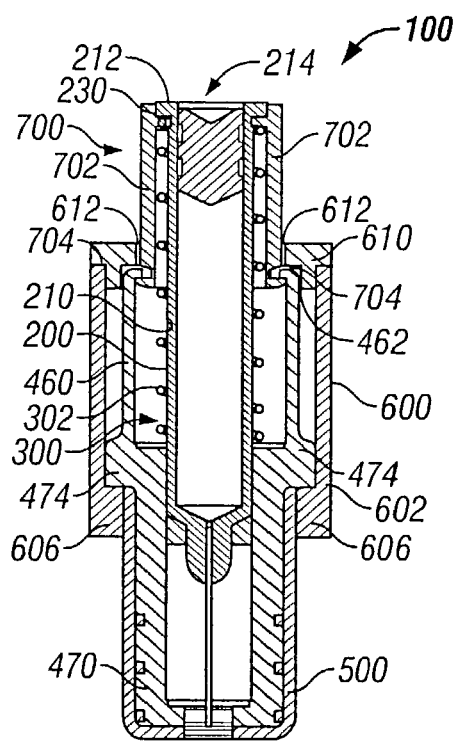
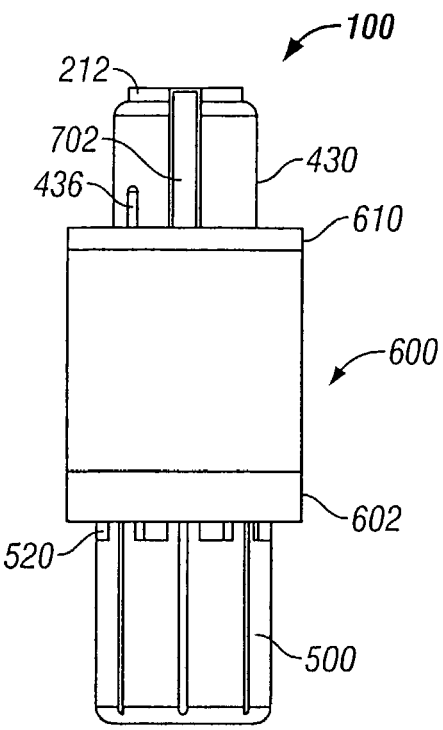
FIG. 11
FIG. 12
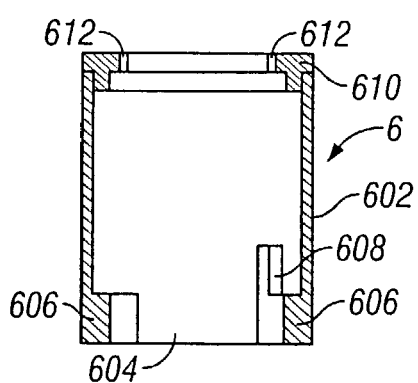
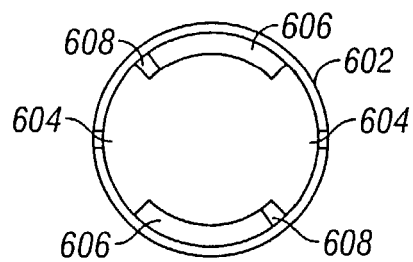
FIG. 14
FIG. 13
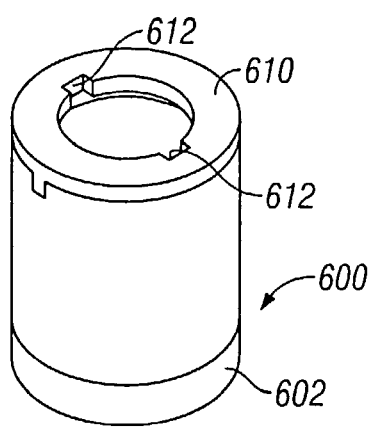
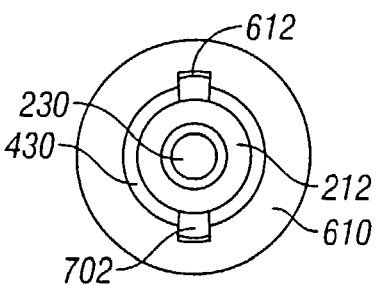
FIG. 15
FIG. 16

COLLAPSIBLE SYRINGE CARTRIDGE

RELATED CASES

This is a non-provisional application claiming priority under 35 U.S.C. § 119 from U.S. provisional application 60/337,681, filed on Nov. 9, 2001.

BACKGROUND

1. Field of the Invention

The present invention relates to syringe cartridges used in injection devices. In particular, the present invention provides a collapsible syringe cartridge that facilitates construction of more compact injection devices and may be designed for use in injection devices generating injection forces sufficient for the delivery of viscous medicaments.

2. State of the Art

Automatic injectors (hereinafter referred to as "autoinjectors") are well known in the medical and veterinary industries and enable the automatic injection of a desired dose of medicament to animal or human subjects. Autoinjectors are thought to exhibit several advantages relative to simple hypodermic syringes. For instance, because autoinjectors may be designed to automatically and reliably deliver a desired dose of medicament on demand, they facilitate quick, convenient, and accurate delivery of medicaments. In particular, autoinjectors are well suited for use by human subjects who must self-administer therapeutic substances.

In order to facilitate storage and delivery of medicament, autoinjectors including a needled injection mechanism generally include a syringe terminating in a needle, such as a hypodermic needle. If desired, the syringe included in an autoinjector may be provided within a syringe cartridge that is permanently or removably mounted to the autoinjector. For example, BD Pharmaceutical Systems of Franklin Lakes, N.J., manufactures the BD™ Auto-Injector, which utilizes a syringe cartridge that is removably mounted to the autoinjector and includes a pre-loaded syringe. Providing the syringe of an autoinjector within a syringe cartridge provides several potential advantages. For example, where the autoinjector is designed or manufactured as a single use device, providing the syringe within a syringe cartridge may ease manufacture of the autoinjector. In addition, where the autoinjector is designed as a multiple use device, providing the syringe of the injector within a cartridge that can be mounted and removed from the device allows a single injector body to be used to carry out multiple injections, to deliver different doses of medicament, or to deliver a range of different medicaments.

However, the syringe cartridges generally known in the art, including the cartridge used in the BD™ Auto-Injector, are not without shortcomings. For instance, state of the art syringe cartridges are typically designed for use with autoinjectors that generate injection forces ranging between about 3 lbs. to 5 lbs. Consequently, state of the art syringe cartridges are typically not suited for use with autoinjectors designed to exert injection forces of sufficient magnitude to deliver viscous medicaments, which may require injection forces exceeding 100 lbs. or more. Moreover, where state of the art syringe cartridges include a mechanism biasing the syringe in a retracted position, the syringe cartridges are typically designed such that the autoinjector must include a plunger having a length equal to or greater than the stroke of the syringe within the syringe cartridge combined with the stroke of the piston within the syringe. Such a requirement adds unnecessary length to the plunger and to the autoinjector itself. Therefore, it would be an improvement in the art to provide a syringe cartridge that is not only suitable for use with autoinjectors capable of delivering viscous medicaments, but is also designed to facilitate the fabrication of a more compact autoinjector.

SUMMARY OF THE INVENTION

The present invention provides a syringe cartridge that is sufficiently robust to be used in autoinjectors that generate injection forces sufficient to deliver viscous medicaments. The syringe cartridge of the present invention includes a syringe, a bias mechanism, and a casing. The casing of the syringe cartridge of the present invention includes a collapsible portion and a fixed portion. Advantageously, the collapsible portion of the casing collapses within the fixed portion of the casing as the syringe is driven through its stroke within the syringe cartridge. As the collapsible portion collapses within the fixed portion, the length of the syringe cartridge is effectively reduced, which, in turn, allows the use of a shorter plunger and thereby facilitates the construction of a more compact autoinjector.

The syringe cartridge of the present invention may also include an adjustable tip. Where included, the adjustable tip engages the distal end of the casing of the syringe cartridge in any manner that permits the adjustable tip to be advanced or retracted relative to the distal end of the casing. Providing the syringe cartridge with an adjustable tip allows the user to easily adjust the injection depth for the desired application.

In order to minimize accidental needle stick injuries, particularly when the syringe cartridge is not mounted to the body of an autoinjector, the syringe cartridge of the present invention may also be designed to include one or more safety mechanisms. For instance, the bias mechanism of the syringe cartridge may be designed to maintain the syringe in a retracted position within the syringe cartridge, unless an insertion force or injection force is applied to the syringe or to the casing. Even further, the syringe cartridge may be designed to include a locking mechanism that works to prevent compression of the syringe cartridge when the syringe cartridge is not mounted to an autoinjector. Such a locking mechanism may be provided in conjunction with an interlock mechanism, which works to prevent accidental locking or unlocking of the locking mechanism. The interlock mechanism may also serve to prevent accidental removal or expulsion of the syringe cartridge from within the body of an autoinjector once the syringe cartridge is properly mounted. Where included in the syringe cartridge of the present invention, the locking mechanism and interlock mechanism are preferably actuated as the syringe cartridge is mounted or removed from the body of an autoinjector.

BRIEF DESCRIPTION OF THE DRAWINGS

FIG. 9 and FIG. 10 provide exploded views of the second syringe cartridge illustrated in FIG. 5 through FIG. 8.

FIGS. 11 and 12 illustrate the syringe cartridge illustrated in FIG. 9 through FIG. 10 positioned within a sleeve including a locking ring and a guide ring.

FIG. 13 through 16 illustrate a sleeve including a guide ring and a locking ring that may be provided within an autoinjector to facilitate mounting and removal of the syringe cartridge illustrated in FIG. 5 through FIG. 10.

DETAILED DESCRIPTION OF THE INVENTION

Figure 1:
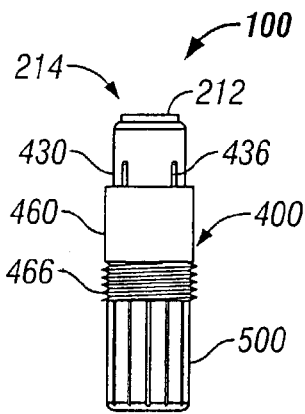
FIG. 1 illustrates a first syringe cartridge of the present invention.
Figure 2:
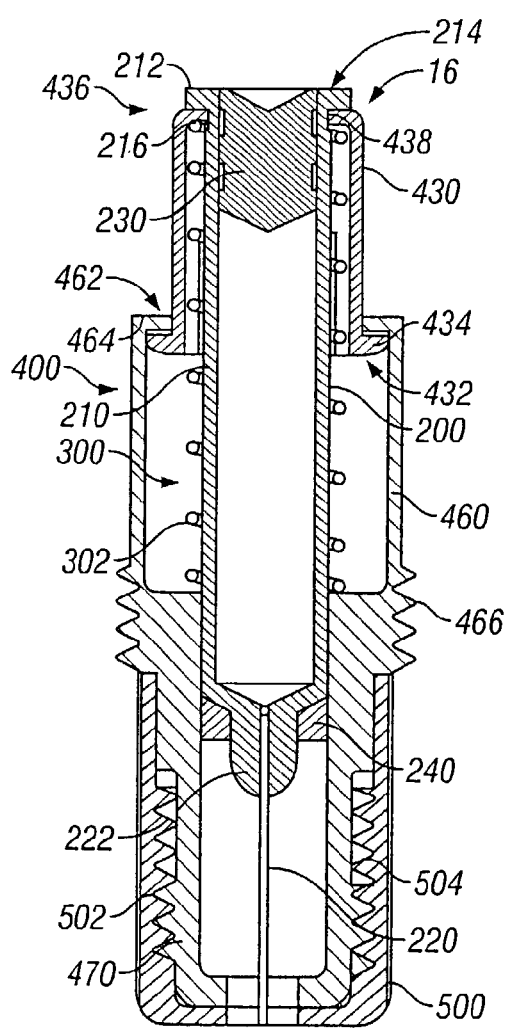
FIG. 2 and FIG. 3 provide cross sectional views of the syringe cartridge illustrated in FIG. 1.

The syringe cartridge 100 of the present invention includes a syringe 200, a bias mechanism 300, and a casing 400. Where desired, the syringe cartridge 100 of the present invention may further include an adjustable tip 500.

The syringe 200 included in the syringe cartridge 100 of the present invention includes a barrel 210, a needle 220, and a piston 230. The syringe 200 may further include a load transfer ring 240 at the distal end 218 of the barrel 210. Where included, the load transfer ring 240 may be constructed of any suitable material, such as a natural or synthetic rubber or polymer material or a metal or metal alloy. The load transfer ring 240 may serve to absorb or dissipate shock as the syringe 200 is driven to the end of its stroke within the syringe cartridge 100. Alternatively, the load transfer ring 240 may simply serve to transfer at least a portion of the load exerted on the barrel 210 of the syringe 200 to the casing 400 of the syringe cartridge.

The barrel 210 of the syringe 200 includes flange 212 at its proximal end 214. The flange 214 facilitates proper placement of the syringe 200 within the syringe cartridge 100. Also at the proximal end 214 of the barrel 210, the syringe 200 may include a seat 216. The seat 216 allows the syringe 200 to be securely mounted to the syringe cartridge 100.

The barrel 210 of the syringe 200 may be constructed of any suitable material, such as a suitable glass, composite, metal, or polymer material. Where the syringe cartridge 100 is to be used to deliver viscous medicaments, it is preferred that the barrel 210 be constructed using a metal or polymer material having sufficient strength to withstand the higher injection forces necessary to deliver viscous medicaments. For example, where the syringe cartridge 100 is to be used to deliver viscous medicaments, the barrel 210 may be constructed using liquid crystal polymer (LCP), PEEK polymer, or stainless steel, such as 304 stainless steel or 316 stainless steel. Moreover, the material used to fabricate the barrel 210 of the syringe 200 should be compatible with the medicament to be loaded within the barrel 210. LCP, PEEK polymer, glass, and stainless steel, such as 304 stainless steel or 316 stainless steel, are exemplary materials that are compatible with a wide range of medicament formulations.

The barrel 210 of the syringe 200 is preferably sized and shaped to ease delivery of the chosen medicament. The barrel 210 may be constructed in any desired size, including standard sizes, but where the syringe cartridge 100 is used to deliver a viscous medicament, the barrel 210 is preferably sized such that the inner diameter of the barrel 210 approximates the gauge of the needle 220 to the extent possible. This is because, according the Hagen-Poiseuille law, the injection force required to drive a medicament from the barrel 210 through the needle 220 increases exponentially as the inner diameter of the barrel 210 increases away from the inner diameter of the needle 220. Of course, the benefits of approximating the inner diameter of the barrel 210 to the inner diameter of the needle 220 must be balanced against other design factors, such as the desired size of the syringe 200 and the volume of medicament to be delivered. In addition, as shown in the figures, the nose 222 of the barrel 210 may be shortened in order to reduce the force required to deliver the chosen medicament. As the nose 222 is shortened, the length of the needle 220 required to achieve a desired injection depth is also reduced, which, in turn, reduces the force required to deliver the medicament from the barrel 210 through the needle 220.

The needle 220 included in the syringe 200 of the syringe cartridge 100 of the present invention may be any needle suitable for the delivery of a desired medicament. For example, the needle 220 may be a hypodermic needle of sufficient length to achieve the subcutaneous, intramuscular, or intra-articular injection of a desired medicament. Of course, the needle 220 may be of any desired length or gauge.

The casing 400 of the injection cartridge 100 of the present invention includes a collapsible portion 430 and a fixed portion 460. The collapsible portion 430 of the casing 400 is sized such that it can be displaced into and out of the fixed portion 460 of the casing 400. To ease positioning of the collapsible portion 430 within the fixed portion 460 of the casing 400, the collapsible portion may be provided with one or more compression grooves 436. The collapsible portion 430 also includes a mechanism that works to ensure that the collapsible portion 430 is not entirely displaced from the fixed portion 460 once the collapsible portion 430 is positioned within the fixed portion 460. For example, the distal end 432 of the collapsible portion 430 may include a first lip 434 that engages a second lip 464 formed at the proximal end 462 of the fixed portion 460 as the collapsible portion 430 extends out of the fixed portion 460.

Figure 3:
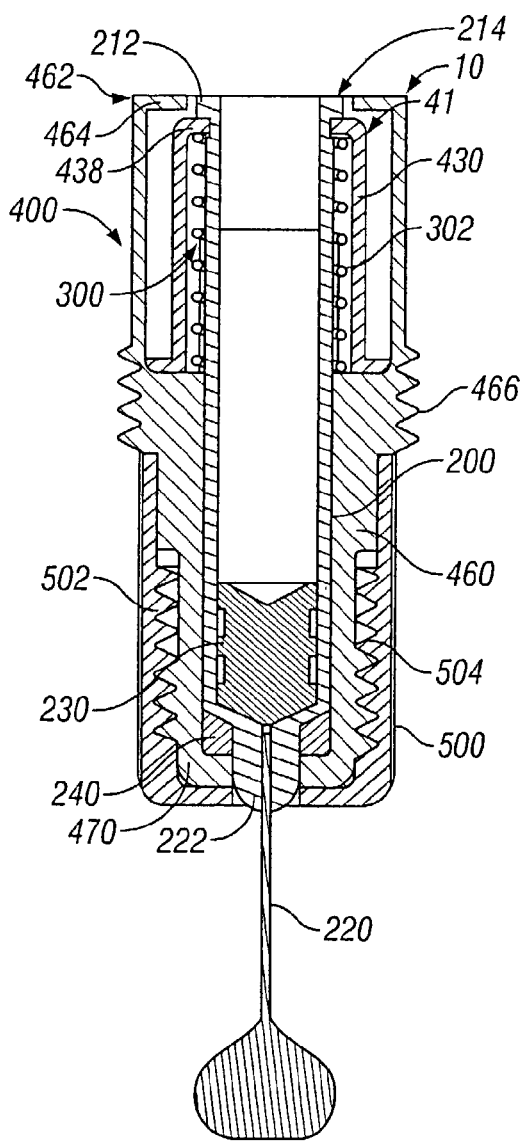

The proximal end 436 of the collapsible portion 430 includes an orifice 438 sized to permit positioning of the syringe 200 within the syringe cartridge 100. As the syringe 200 is positioned through the orifice 438, the proximal end 436 of the collapsible portion 430 engages the seat 216 included in the barrel 210 of the syringe 200, thereby providing a snap-fit connection between the syringe 200 and the casing 400. To ease positioning of the syringe 200 within the collapsible portion 430 of the casing 400, the orifice 438 may include one or more expansion groves 440, which allow the orifice 438 expand as the syringe 200 is being positioned through the orifice 438. The orifice 438 is also sized to engage the flange 212 formed at the proximal end 214 of the barrel 210 of the syringe 200 as the syringe 200 is positioned through the orifice 438. Thus, as the syringe 200 is advanced or retracted within the syringe cartridge 100, the collapsible portion 430 of the casing 400 collapses within or extends out of the fixed portion 460 of the casing 400. FIG. 1, FIG. 2, and FIG. 4 through FIG. 12 illustrate the syringe 200 in a retracted position, while FIG. 3 illustrates the syringe 200 in an advanced position.

In the embodiments illustrated herein, the bias mechanism 300 of the syringe cartridge 100 of the present invention includes a coil spring 302. The coil spring 302 maintains the collapsible portion 430 in a normally extended position, which corresponds to the retracted position of the syringe 200. Instead of a coil spring 302, however, the bias mechanism 300 of the syringe cartridge 100 of the present invention may include any other suitable biasing member, such as a solid or foamed rubber or polymer bumper, or a fluid filled, resilient bladder. The spring rate or force required to compress the bias mechanism 300 may be varied, as desired, provided that such spring rate or force is at least sufficient to bias the syringe 200 in a retracted position, until an insertion or injection force is applied to the syringe 200. Once an insertion or injection force terminates, however, the bias mechanism 300 automatically retracts the syringe 200 back within the casing 400.

So that the syringe cartridge 100 of the present invention can be mounted within a autoinjector, the fixed portion 460 of the casing 400 of the syringe cartridge 100 is provided with a mounting mechanism. For example, the fixed portion 460 of the casing 400 may include a first threaded area that is complimentary to a second threaded area provided within the body of the autoinjector (shown in FIG. 1 through FIG. 4). Alternatively, the fixed portion 460 of the casing 400 of the syringe cartridge 100 may include one or more locking tabs (shown in FIG. 5 through FIG. 7 and FIG. 9 through FIG. 11) complimentary to a locking ring formed within the body of the autoinjector or within an adapter that may be mounted within the autoinjector. Though the figures provided herein show syringe cartridges 100 including one of two specific mounting mechanisms, the syringe cartridge 100 of the present invention may incorporate any other suitable mounting mechanism.

FIG. 1 through FIG. 4 illustrate a first embodiment of the syringe cartridge 100 of the present invention. Though the first embodiment of the syringe cartridge 100 of the present invention may be used in conjunction with a multi-use injection device, the syringe cartridge 100 of the first embodiment is particularly suited for use with a single-use or disposable injection device.

As is easily appreciated in FIG. 1 through FIG. 4, the first embodiment of the syringe cartridge 100 of the present invention is designed to be threaded into the body 12 of an autoinjector 10. The fixed portion 460 of the casing 400 of the syringe cartridge of the first embodiment includes a first threaded area 466 that is complimentary to a second threaded area 468 provided within the body 12 of the autoinjector 10. The first and second threaded areas 466, 468 enable quick and easy mounting of the syringe cartridge to the body 12 of the autoinjector 10, while providing a robust mounting mechanism capable of withstanding even the large injection forces that may be required for the delivery of viscous medicaments.

The syringe cartridge 100 of the first embodiment also includes an adjustable tip 500. The adjustable tip 500 of the first embodiment includes a first threaded area 502 that is complimentary to a second threaded area 504 formed on the distal end 470 of the fixed portion 460 of the casing 400. The first and second complimentary threaded areas 502, 504 allow the adjustable tip 500 to be advanced or retracted relative to the distal end 470 of the casing 400, thereby allowing the user to adjust the penetration depth of the needle 220. The first and second threaded areas 502, 504 preferably provide a threading mechanism that is threaded in the opposite direction as the threading mechanism utilized to mount the syringe cartridge 100 of the first embodiment to the body 12 of an autoinjector 10. For example, where the syringe cartridge 100 is mounted to the body 12 of an autoinjector 10 using a "right handed" threading mechanism, the first and second threaded areas 502, 504 formed in the adjustable tip 500 and the distal end 470 of the casing 400 preferably form a "left handed" threading mechanism. Though FIG. 1 through FIG. 4 illustrate an adjustable tip 500 that engages the distal end 470 of the fixed portion 460 of the casing 400 via a threading mechanism, the adjustable tip 500 may engage the distal end 470 using any other suitable mechanism, such as a ratchet-fit mechanism or snap-fit mechanism, that allows the adjustable tip 500 to be advanced or retracted relative to the distal end 470 of the fixed portion 460 of the casing 400.

Figure 4:
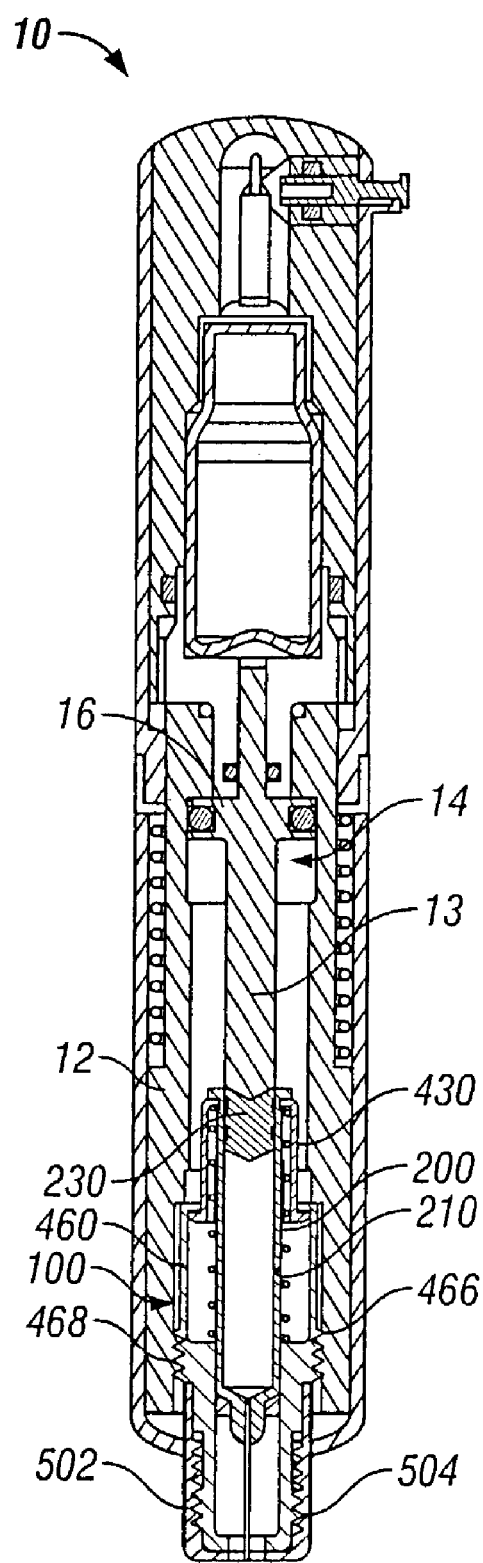
FIG. 4 illustrates an exemplary autoinjector incorporating a syringe cartridge of the present invention.

FIG. 4 illustrates a pneumatic autoinjector 10 having a syringe cartridge 100 according to the first embodiment mounted thereto. As can be appreciated by reference to FIG. 4, the autoinjector 10 includes a dual stage driving mechanism that sequentially exerts an insertion force and an injection force against the syringe 200 included in the syringe cartridge 100. The insertion and injection forces generated by the driving mechanism of the autoinjector 10 are transmitted to the piston 230 of the syringe 200 via a plunger 13 formed at the distal end 14 of a two-stage piston 16 included in the driving mechanism of the autoinjector 10. Upon exertion of the an insertion force, the syringe 200 is driven against the bias mechanism 300 to an advanced position within the syringe cartridge 100, causing the collapsible portion 430 of the casing 400 to collapse within the fixed portion 460 of the casing 400. Because the collapsible portion 430 of the casing 400 is driven within the fixed portion 460 of the casing 400 as the syringe 200 is advanced within the syringe cartridge 100, the plunger 13 formed at the distal end 14 of the two-stage piston 16 need only be long enough to drive the piston 230 of the syringe 200 through its stroke within the syringe barrel 210. In contrast, however, if the syringe cartridge 100 did not include a collapsible casing, the plunger 13 would need to have a length equal to or greater than the stroke of the syringe 200 within the syringe cartridge 100 combined with the stroke of the piston 230 within the syringe barrel 210 in order for the autoinjector 10 to effect both insertion of the needle 220 within a subject and injection of the medicament contained within the syringe 200.

A second embodiment of the syringe cartridge 100 of the present invention is illustrated in FIG. 5 through FIG. 12. Though the syringe cartridge 100 of the second embodiment may be used in conjunction with a single-use or disposable injection device, the second embodiment of the syringe cartridge 100 of the present invention is particularly suited for use with a multiple-use injection device.

The second embodiment of the syringe cartridge 100 of the present invention is mounted to the body of an injector via one or more locking tabs 474. The locking tabs 474 engage a locking ring 602 that may be integrated into the body of the autoinjector (not shown) or provided as part of a sleeve 600 to be positioned within the body of an autoinjector (shown in FIG. 11 through FIG. 15). Though it is not illustrated herein, it is presently preferred to form the locking ring 602 as an integral part of the body of the autoinjector to which the syringe cartridge 100 is to be mounted. Such a design not only simplifies the design of the autoinjector, but also serves to reduce the diameter of the autoinjector.

As is easily seen in FIG. 13 and FIG. 14, the locking ring 602 includes one or more passages 604 and one or more locking members 606, which include a vertical stop 608. In order to mount a syringe cartridge 100 according to the second embodiment using the locking ring 602, the syringe cartridge 100 advanced through the locking ring 602 until the locking tabs 474 of the syringe cartridge 100 pass within or through the one or more passages 604 of the locking ring and are positioned to engage the one or more locking members 606 of the locking ring 602. To ease proper positioning of the syringe cartridge 100, the autoinjector to which the syringe cartridge 100 is to be mounted may be designed such that the syringe cartridge 100 abuts a mechanical stop when the locking tabs 474 are properly positioned to engage the locking members of the locking ring 602. Such a mechanical stop may be provided, for example, by the plunger of the autoinjector. Once the syringe cartridge is properly positioned relative to the locking ring 602, a torque is applied to the syringe cartridge 100 until the locking tabs 474 of the syringe cartridge 100 engage the one or more locking members 606 and reach the vertical stops 608. FIG. 11 provides a cross sectional view of a syringe cartridge 100 according to the second embodiment mounted within a sleeve 600, wherein the locking tabs 474 of the syringe cartridge 100 have engaged the locking members 606 of the locking ring 602.

The second embodiment of the syringe cartridge 100 of the present invention includes a locking mechanism 700, which serves to minimize accidental compression of the syringe cartridge 100 when the syringe cartridge 100 is not mounted to an injector. As shown in FIG. 5 through FIG. 12, the locking mechanism may include one or more ears 702 extending away from the outer surface 442 of the collapsible portion 430 of the casing 400. When the syringe cartridge 100 is placed in a locked position, the one or more ears 702 cannot pass through the proximal end 462 fixed portion 460 of the casing 400, thereby preventing the collapsible portion 430 from being compressed within the fixed portion 460. In an unlocked position, the one or more ears 702 are aligned with one or more passages 704 formed in the proximal end 462 of the fixed portion 460 of the casing 400. The one or more passages 704 allow the one or more ears 702 to pass through the proximal end 462 of the fixed portion 460 of the casing 400 and thereby allow the collapsible portion 430 to be compressed within the fixed portion 460. Preferably, the syringe cartridge 100 and the injector to which the syringe cartridge 100 is to be mounted are designed such that the syringe cartridge is placed in the unlocked position when mounted to the injector but returned to the locked position when removed from the injector.

To provide actuation of the locking mechanism 700 upon mounting and removing of a syringe cartridge 100 according to the second embodiment to an autoinjector, the autoinjector may include a guide ring 610. Like the locking ring 602, the guide ring 610 may be integrated into the body of an autoinjector (not shown) or included in a sleeve 600 that is to be positioned within the body of an autoinjector, as is shown in FIG. 11 through FIG. 15. Though it is not illustrated herein, it is presently preferred to form the guide ring 610 as an integral part of the body of the autoinjector to which the syringe cartridge 100 is to be mounted. Such a design not only simplifies the design of the autoinjector, but also serves to reduce the diameter of the body of the autoinjector.

As can be seen in the figures, the guide ring 610 includes one or more guide slots 612 that are sized to receive the one or more ears 702 of the locking mechanism. As a syringe cartridge 100 is advanced through the locking ring 602, the ears 702 of the locking mechanism are positioned within the one or more guide slots 612. Once the ears 702 of the locking mechanism 700 are positioned within the one or more guide slots 612 and the syringe cartridge 100 is properly positioned within the locking ring 602, a torque is applied to engage the locking members 606 of the locking ring 602 with the locking tabs 474 of the casing 400. Because the guide ring 610 is fixed in position and the ears 702 of the locking mechanism are held in place by the guide slots 612, application of the torque necessary to engage the locking members 606 with the locking tabs 474 causes the fixed portion 460 of the casing 400 to rotate relative to the collapsible portion 430 of the casing 400.

The guide ring 610 is positioned relative to the locking ring 602 such that only a locked syringe cartridge 100 can be advanced through or withdrawn from the locking ring 602. When a locked syringe cartridge 100 according to the second embodiment is mounted to an autoinjector using the guide ring 610 and locking ring 602 described herein, the rotation of the collapsible portion 430 relative to the fixed portion 460 aligns the one or more ears 702 of the locking mechanism 700 with the one or more passageways 704 of the locking mechanism 700. Because of the vertical stops 608 provided in the locking ring 602, once a syringe cartridge 100 is mounted to an autoinjector including a locking ring 602 and guide ring 610, an opposite torque must be applied to remove the syringe cartridge 100 from the locking ring 602. As this opposite torque is applied, the collapsible portion 430 of the casing rotates again relative to the fixed portion 460 of the casing 400, and such rotation brings the ears 702 and passageways 704 of the locking mechanism 700 out of alignment. Therefore, where an autoinjector is provided with a locking ring 602 and guide ring 610 as illustrated in FIG. 11 through FIG. 15, the autoinjector is easily configured so that the act of mounting a syringe cartridge 100 according to the second embodiment inherently moves the locking mechanism 700 from a locked to an unlocked position and the act of removing a syringe cartridge 100 according to the second embodiment inherently moves the locking mechanism 700 from an unlocked to a locked position.

Where desired, the second embodiment may be further provided with an interlock mechanism 800. An interlock mechanism 800 may serve not only to minimize accidental actuation of the locking mechanism 700, but may also serve to minimize the possibility of accidental removal or expulsion of a syringe cartridge 100 from an autoinjector 100 once the syringe cartridge 100 is mounted thereto. FIG. 5, FIG. 6, FIG. 9, and FIG. 10 best illustrate an interlock mechanism 800 that may be included in the syringe cartridge 100 of the present invention.

The interlock mechanism 800 shown in FIG. 5, FIG. 6, FIG. 9, and FIG. 10 utilizes the bias force exerted by the bias mechanism 300 and includes one or more interlock tabs 802 together with one or more first interlock spaces 804 and one or more second interlock spaces 806. The interlock tabs 802 are formed on the first lip 434 of the collapsible portion 430 of the casing 400, and the first and second interlock spaces 804, 806 are formed in the second lip 464 of the fixed portion 460 of the casing 400. In the embodiment illustrated in FIG. 5, FIG. 6, FIG. 9, and FIG. 10, the passageways 704 formed at the proximal end 462 of the fixed portion 460 of the casing 400 also serve as the first interlock spaces 804 of the interlock mechanism 800.

Figure 5:
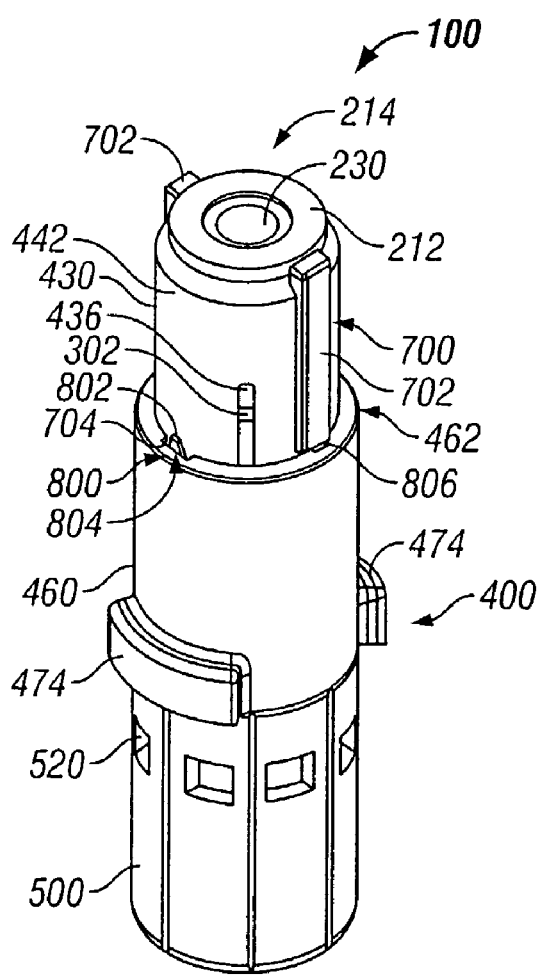
FIGS. 5 and FIG. 6 illustrate a second syringe cartridge according to the present invention.
Figure 6:
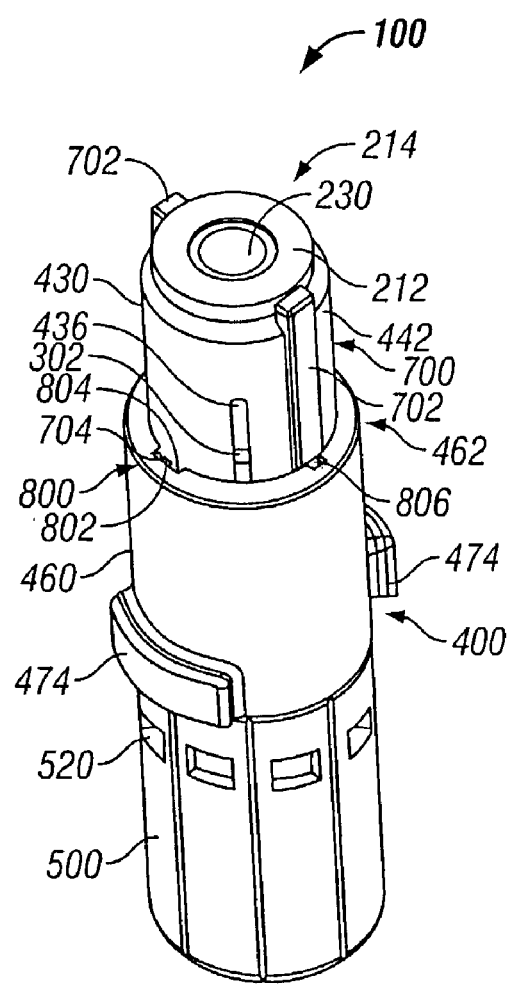
Figure 7:
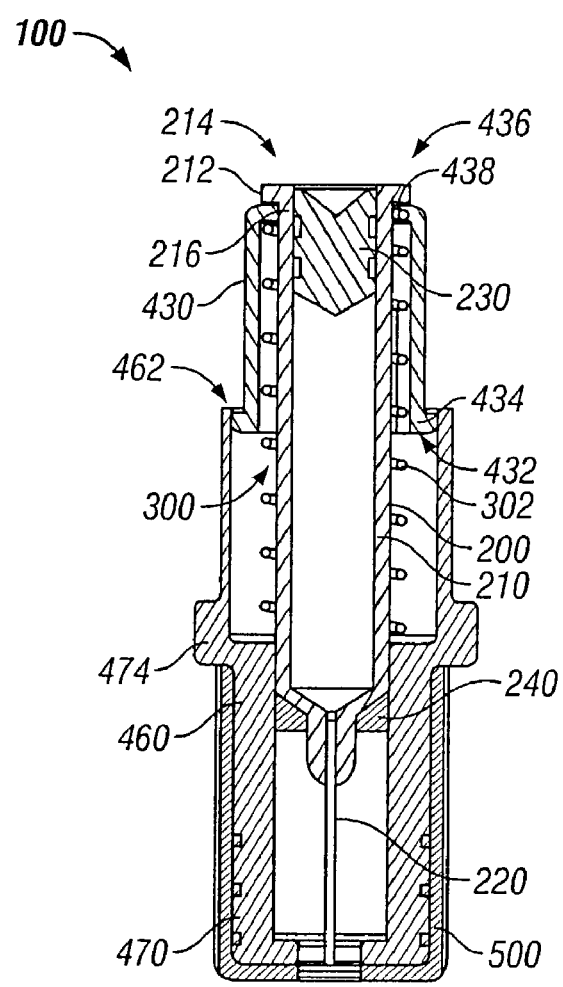
FIG. 7 and FIG. 8 provide cross sectional views of the syringe cartridge illustrated in FIG. 5 and FIG. 6.
Figure 8:
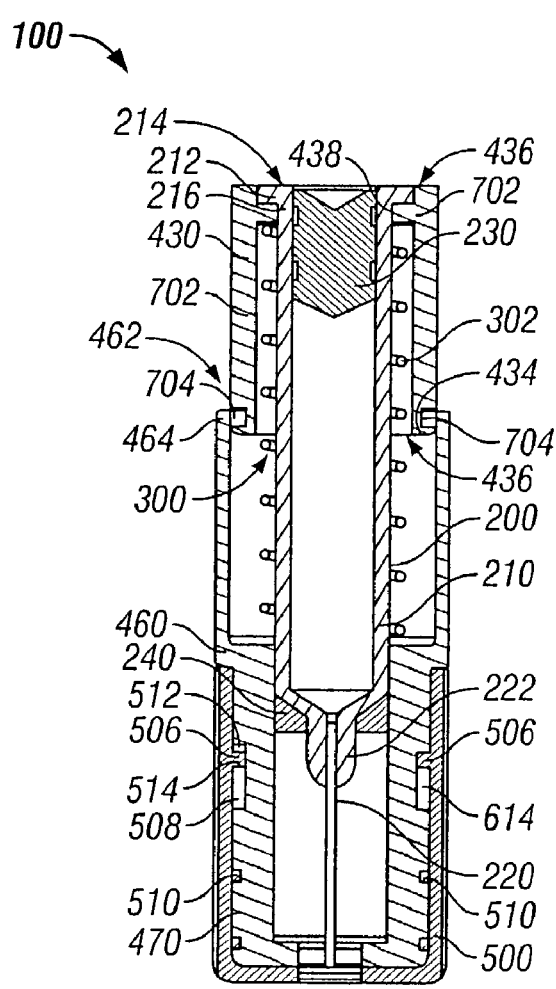

FIGS. 5 and 6 illustrate the interlock tabs 802 of the interlock mechanism 800 positioned within the first interlock spaces 804. As is easily appreciated from the figures, when the interlock tabs are positioned within the first interlock spaces 804, the locking mechanism 700 of the syringe cartridge 100 is in a locked position. The bias force exerted by the bias mechanism 300 maintains the interlock tabs 802 within the first interlock spaces 804 until a torque is applied together with a compressive force sufficient to overcome the bias force exerted by the bias mechanism 300. Therefore, the interlock mechanism 800 serves to lock the locking mechanism 700 of the syringe cartridge 100 in a locked position until both a torque and a compressive force sufficient to overcome the bias mechanism 300 are simultaneously applied.

Once the appropriate combination of torque and compressive force is applied, the interlock tabs 802 may be displaced from the first interlock spaces 804, and the collapsible portion 430 of the casing 400 may be rotated such that the locking mechanism 700 is placed in an unlocked position. As the collapsible portion 430 is rotated and the interlock tabs 802 reach the second interlock spaces 806, the bias force exerted by the bias mechanism 300 causes the interlock tabs 802 to engage the second interlock spaces 806. As can be seen in FIG. 5 and FIG. 6, when the interlock tabs 802 are positioned within the second interlock spaces 806, the locking mechanism 700 is placed in an unlocked position (i.e., the ears 702 and passageways 704 of the locking mechanism 700 are aligned). Once the interlock tabs 802 are positioned within the second interlock spaces 806, the bias force exerted by the bias mechanism 300 serves to maintain the interlock tabs 802 within the second interlock spaces 806 until an appropriate combination of torque and compressive force is again applied. Therefore, the interlock mechanism 800 may not only serve to retain the locking mechanism 700 of the syringe cartridge 100 in a locked position, but the interlock mechanism 800 may also be designed to retain the locking mechanism 700 of the syringe cartridge 100 in an unlocked position once such position is attained.

Advantageously, the interlock mechanism 800 illustrated in FIG. 5, FIG. 6, FIG, 9, and FIG. 10 is easily actuated by mounting and removing the syringe cartridge 100 according to the second embodiment to and from an autoinjector including a locking ring 602 and a guide ring 610, as described herein. As the syringe cartridge 100 is mounted to an autoinjector including a locking ring 602 and guide ring 610, the syringe cartridge 100 is advanced through the locking ring 602 and into the guide ring 610 until the syringe cartridge 100 abuts a mechanical stop. Again, the mechanical stop may be provided, for example, by the plunger of the autoinjector. Once the mechanical stop is reached a compressive force sufficient to overcome the bias mechanism 300 and a first torque are simultaneously applied to the syringe cartridge 100, causing the interlock tabs 802 to be displaced from the first interlock spaces 804. Such action allows the fixed portion 460 of the casing 400 to be rotated relative to the collapsible portion 430 of the casing 400 so that the locking tabs 474 of the casing 400 may engage the locking members 606 of the locking ring 602. As the fixed portion 460 of the casing is rotated and the locking tabs 474 reach the vertical stops 608 of the locking members 606, the interlock tabs 802 engage the second interlock spaces 806, and the bias force exerted by the bias mechanism 300 maintains the interlock tabs 802 within the second interlock spaces 806. Therefore, once the syringe cartridge 100 is properly mounted within an autoinjector, the interlock mechanism 800 retains the locking mechanism 700 of the syringe cartridge 100 in an unlocked position. Moreover, because the mechanical stop created by the interlock tabs 802 positioned within the second interlock spaces 806 prevents rotation of the fixed portion 460 of the casing 400 relative to the collapsible portion 430 of the casing 400, the interlock mechanism 800 also serves to prevent accidental removal or expulsion of a syringe cartridge 100 properly mounted to an autoinjector.

In order to remove a syringe cartridge 100 including an interlock mechanism 800 from an autoinjector including a locking ring 602 and a guide ring 610, the interlock mechanism 800 must be actuated to allow rotation of the fixed portion 460 of the casing 400 relative to the collapsible portion 430 of the casing 400. Actuation of the interlock mechanism 800 is simply carried out through the simultaneous application of a compressive force sufficient to overcome the bias mechanism 300 and a second torque (carried out in the direction opposite the first torque) such that the interlock tabs 802 are displaced from the second interlock spaces 806. Once the interlock tabs 802 are displaced from the second interlock spaces 806, the fixed portion 460 of the casing may be rotated relative to the collapsible portion 430. As the fixed portion 460 is rotated to disengage the locking tabs 474 of the casing 400 from the locking members 606 of the locking ring 602, the interlock tabs 802 approach and engage the first interlock spaces 804, which locks the locking mechanism 700 of the syringe cartridge 100 in a locked position as the syringe cartridge 100 is removed from the autoinjector.

The syringe cartridge 100 according to the second embodiment also includes an adjustable tip 500. Like the adjustable tip 500 of the first embodiment, the adjustable tip 500 of the syringe cartridge 100 of the second embodiment may engage the distal end 470 of the casing 400 using any mechanism that allows the adjustable to be advanced or retracted along the distal end 470 of the casing 400. For instance, the adjustable tip may 500 may engage the distal end 470 of the casing using a ratchet-fit mechanism, a snap-fit mechanism, or a threading mechanism.

The adjustable tip 500 illustrated in FIG. 5 through FIG. 12 utilizes a threading mechanism to engage the distal end 470 of the casing 400. The threading mechanism includes one or more threading pins 506 formed on the interior surface 508 of the adjustable tip 500 and one or more threads 510 formed in the distal end 470 of the casing 400. The threading pins 506 are positioned on the adjustable tip such that, upon the application of a torque to the adjustable tip 500, the threading pins 506 are guided within the one or more threads 510 and the adjustable tip 500 is either advanced or retracted relative to the distal end 470 of the casing 400. Where the syringe cartridge of the second embodiment is mounted to an autoinjector using a right-handed torque, the adjustable tip 500 is preferably threaded onto the distal end 470 of the casing 400 using a left-handed torque.

Where the syringe cartridge 100 of the present invention includes an adjustable tip 500 having a threading mechanism including one or more threading pins 506 and one or more threads 510, each of the threads 510 may terminate in a locking area 512 including a locking pin 514, as is shown in FIG. 7 through FIG. 10. As the adjustable tip 500 is fully retracted and the threading pins 506 reach the terminus of the corresponding thread 510, the threading pins 506 maybe locked into the locking area 512 by applying a force to the adjustable tip 500 that causes the threading pins 506 to be displaced over the locking pins 514 and into a locked position within the locking areas 512. To release the threading pins 506 from the locking areas 512, the adjustable tip 500 is pulled, forcing the threading pins 506 back over the locking pins 514 and into an unlocked position within their corresponding threads 510. Locking the threading pins 506 within the locking areas 512 facilitates mounting and removal of the syringe cartridge 100 of the present invention to an autoinjector without advancing or retracting the adjustable tip 500 relative to the distal end 470 of the casing 400.

Where the syringe cartridge 100 of the present invention includes an adjustable tip 500, the adjustable tip 500 or the distal end 470 of the casing 400 may be provided with any suitable indicator or series of indicators that allow the user to select a desired injection depth. For example, as is shown in FIG. 5, FIG. 6, and FIG. 9 through FIG. 12, the adjustable tip may be provided with one or more windows 520 that allow a user to observe one or more injection depth indicators, such as numbers, letters, words, colors, icons or any other indicator that may be used to indicate one or more injection depths, provided on the distal end 470 of the casing 400. Alternatively, the adjustable tip 500 may be made of a transparent or translucent material that allows a user to observe one or more injection depth indicators provided on the distal end 470 of the casing 400. Further still, the distal end 470 of the casing 400 may include one or more injection depth indicators that are observable only as the adjustable tip 500 is advanced to a position or positions corresponding to the indicated injection depth.

The various components of the syringe cartridge 100 may be constructed using any suitable material. For instance, one or more components of the syringe cartridge 100 of the present invention may be fabricated using a suitable glass, composite, metal, or polymer material. Where it is anticipated that the syringe cartridge 100 of the present invention will be used for the injection of a viscous medicament, the casing 400 of the syringe cartridge 100 will generally be constructed using a metal, composite, or polymer material, such as LCP, PEEK polymer, or Delryn polymer, that is capable of withstanding the stresses produced as the required injection force is applied.

Advantageously, the syringe cartridge of the present invention may be used in any injection device, which utilizes a plunger to drive medicament through a needled injection mechanism. Though only a pneumatic autoinjector is illustrated herein, those of skill in the art will readily appreciate that the syringe cartridge of the present invention is suited for use in conjunction with an autoinjector including any desired driving mechanism. For example, the syringe cartridge of the present invention may be used with an autoinjector including a spring-loaded driving mechanism, an electromechanical driving mechanism, or even a driving mechanism including a chemical engine. Moreover, though the figures herein illustrate an embodiment of the syringe cartridge according to the present invention mounted to an autoinjector including a dual stage driving mechanism (i.e., the driving mechanism exerts an insertion force and an injection force), those of skill in the art will appreciate that the syringe cartridge of the present invention is equally useful in conjunction with autoinjectors including single stage driving mechanisms (i.e., driving mechanisms capable of generating only an injection force).

What is claimed is:

1. A syringe cartridge comprising:
   a syringe with an associated needle; and
   a casing exhibiting a first length that includes a fixed portion and a collapsible portion, wherein the syringe is positioned through the collapsible portion of the casing, and the syringe, the fixed portion of the casing and the collapsible portion of the casing are configured such that, upon application of a force to the syringe, the collapsible portion of the casing is motivated into the fixed portion of the casing and the first length of the casing is reducible to the length of the fixed portion.

2. The syringe cartridge of claim 1, further comprising a bias member.

3. The syringe cartridge of claim 2, wherein the bias member biases the collapsible portion of the casing in a normally extended position relative to the fixed portion of the casing such that the needle associated with the syringe is normally retracted within the fixed portion of the casing.

4. The syringe cartridge of claim 2, wherein the bias member is selected from a group consisting of a spring, a fluid filled bladder, and a natural or synthetic rubber or polymer material.

5. The syringe cartridge of claim 1, wherein the casing further comprises a mounting mechanism configured to allow the syringe cartridge to be removably mounted to an injection device.

6. The syringe cartridge of claim 1, wherein the casing further comprises a first set of threads complimentary to a second set of threads included in an injection device.

7. The syringe cartridge of claim 6, wherein the first and second sets of complimentary threads are configured to allow the syringe cartridge to be removably mounted within the injection device.

8. The syringe cartridge of claim 1, wherein the casing further comprises one or more locking tabs that are complimentary to a locking ring included in an injection device.

9. The syringe cartridge of claim 8, wherein the one or more locking tabs and the complimentary locking ring are configured to allow the syringe cartridge to be removably mounted within the injection device.

10. The syringe cartridge of claim 1, wherein the fixed portion of the casing further comprises an adjustable tip.

11. The syringe cartridge of claim 1, further comprising a mechanism configured to lock the collapsible portion of the casing relative to the fixed portion of the casing such that movement of the collapsible portion of the casing within the fixed portion of the casing is prevented.

12. The syringe cartridge of claim 1, further comprising:
    a locking mechanism configured to transition between a locked position, wherein movement of the collapsible portion of the casing within the fixed portion of the casing is prevented, and an unlocked position, wherein movement of the collapsible portion of the casing within the fixed portion of the casing is permitted; and
    an interlock mechanism configured to maintain the locking mechanism in the locked position as the locked position is achieved or in the unlocked position as the unlocked position is achieved.

13. The syringe cartridge of claim 1, further comprising:
    a locking mechanism configured to transition between a locked position, wherein movement of the collapsible portion of the casing within the fixed portion of the casing is prevented, and an unlocked position, wherein movement of the collapsible portion of the casing within the fixed portion of the casing is permitted;
    an interlock mechanism configured to maintain the locking mechanism in the locked position as the locked position is achieved or in the unlocked position as the unlocked position is achieved; and
    a mounting mechanism configured to allow the syringe cartridge to be mounted to an injection device.

14. The syringe cartridge of claim 1, further comprising:
    a locking mechanism configured to transition between a locked position, wherein movement of the collapsible portion of the casing within the fixed portion of the casing is prevented, and an unlocked position, wherein movement of the collapsible portion of the casing within the fixed portion of the casing is permitted;
    an interlock mechanism configured to maintain the locking mechanism in the locked position as the locked position is achieved or in the unlocked position as the unlocked position is achieved; and
    a mounting mechanism by which the syringe cartridge can be mounted to an injection device, the mounting mechanism being configured such that mounting of the syringe cartridge to the injection device facilitates actuation of the interlock mechanism and transitions the interlocking mechanism from the locked position to the unlocked position.

15. The syringe cartridge of claim 1, further comprising a locking mechanism configured to transition between a locked position, wherein movement of the collapsible portion of the casing within the fixed portion of the casing is prevented, and an unlocked position, wherein movement of the collapsible portion of the casing within the fixed portion of the casing is permitted.

16. The syringe cartridge of claim 15, wherein the locking mechanism is configured such that the locking mechanism can be transitioned between the locked and unlocked positions through rotational movement of the collapsible portion of the casing relative to the fixed portion of the casing.

17. The syringe cartridge of claim 1, wherein the collapsible portion of the casing includes one or more members extending away from an outer surface of the collapsible portion, the fixed portion of the casing includes one or more passages complimentary to the one or more members included on the outer surface of the collapsible portion, and the fixed and collapsible portions of the casing are configured such that, when the one or more members included on the outer surface of the collapsible portion are aligned with the one or more passages complimentary to the one or more members, the collapsible portion of the casing can be motivated into the fixed portion of the casing.

18. The syringe cartridge of claim 17, wherein the collapsible portion of the casing and the fixed portion of the casing are configured such that, when the one or more members included on the outer surface of the collapsible portion are not aligned with the one or more passages complimentary to the one or more members, the collapsible portion of the casing can not be motivated into the fixed portion of the casing.

* * * * *